United States Patent [19]

Pittet et al.

[11] Patent Number: 4,515,966

[45] Date of Patent: May 7, 1985

[54] 4,5-DIMETHYL-2-(2-METHYLTHIO)ETHYL)-1,3-OXATHIOLANE

[75] Inventors: Alan O. Pittet, Atlantic Highlands; Thomas F. Courtney, Jr., Oakhurst; Ranya Muralidhara, Fair Haven, all of N.J.

[73] Assignee: International Flavors & Fragrances Inc., New York, N.Y.

[21] Appl. No.: 533,747

[22] Filed: Sep. 19, 1983

[51] Int. Cl.³ .......................................... C07D 327/04
[52] U.S. Cl. .................................... 549/30; 426/535
[58] Field of Search .......................................... 549/30

[56] References Cited
U.S. PATENT DOCUMENTS 4,153,442  5/1979  Clapot et al. ........................... 549/30

Primary Examiner—Henry R. Jiles
Assistant Examiner—J. G. Mullins
Attorney, Agent, or Firm—Arthur L. Liberman

[57] ABSTRACT

Described is the genus of methyl(methylthioethyl)-1,3-dioxolanes and oxathiolanes defined according to the structure:

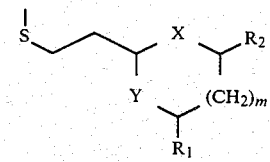

wherein X and Y represent sulphur or oxygen with the proviso that at least one of X and Y is oxygen; wherein m is 0 or 1; and wherein $R_1$ and $R_2$ are the same or different and each represent hydrogen or methyl and uses of such methyl(methylthioethyl)-1,3-dioxolanes and oxathiolanes in augmenting or enhancing the aroma or taste of foodstuffs.

1 Claim, 11 Drawing Figures

FIG.1
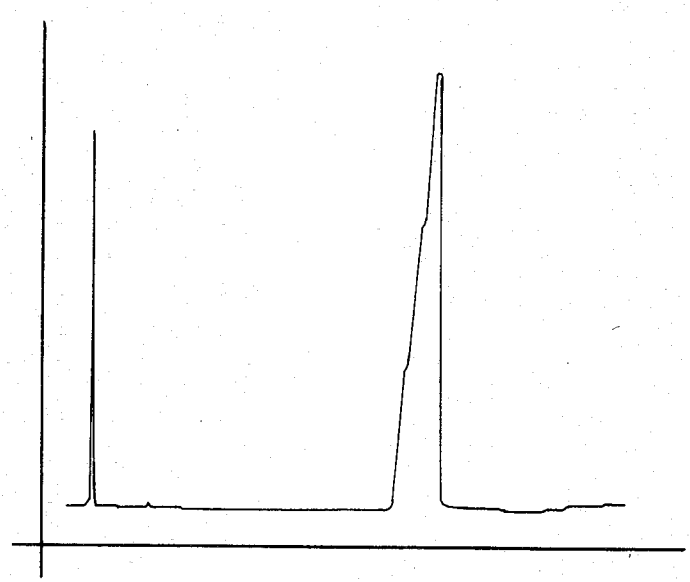
GLC PROFILE FOR FRACTION 3
OF EXAMPLE I.
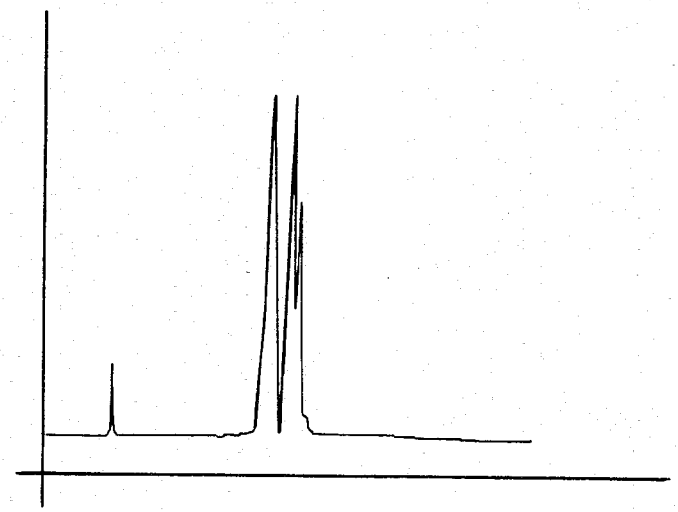
GLC PROFILE FOR FRACTION 3
OF EXAMPLE II.
FIG.3

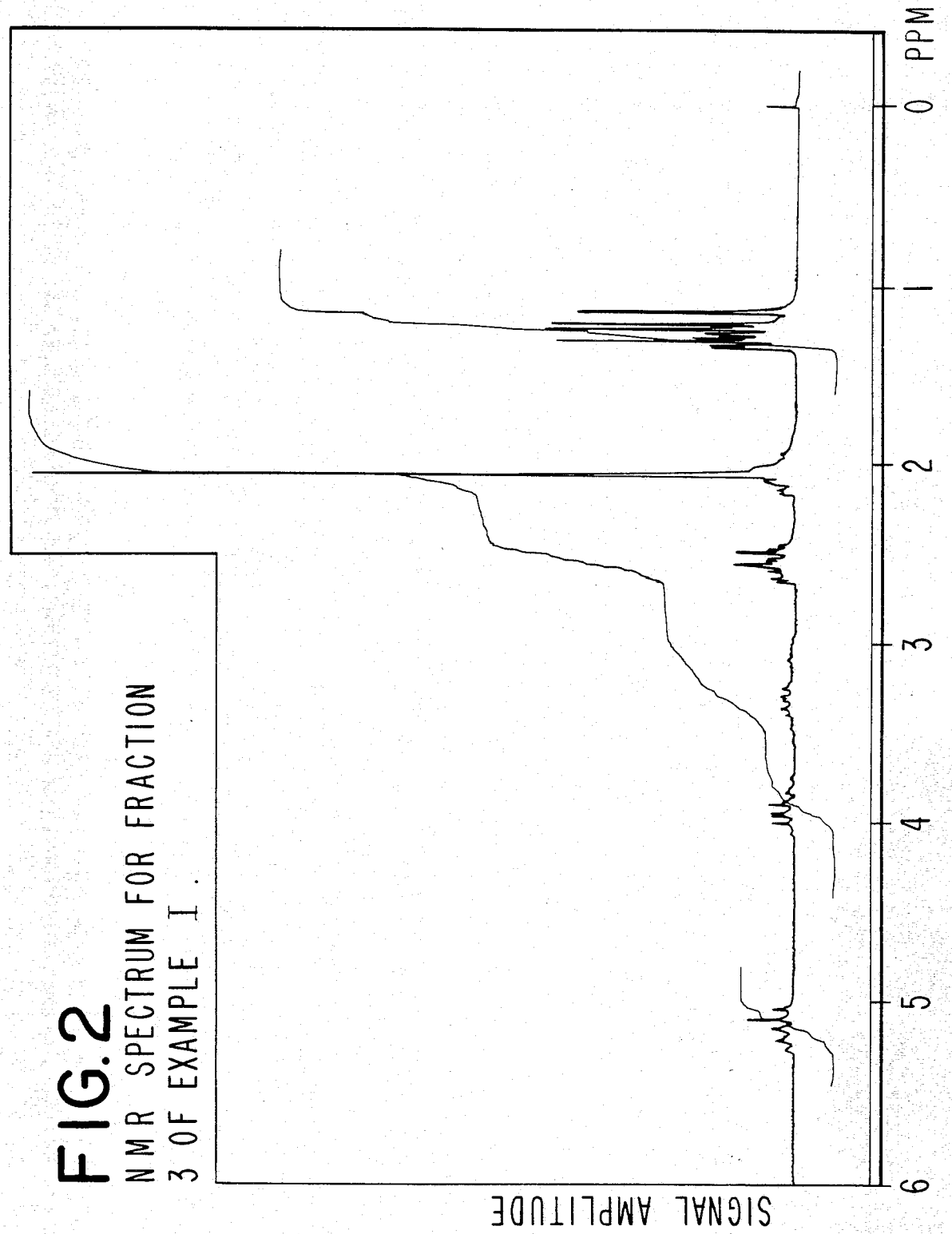
FIG. 2 NMR SPECTRUM FOR FRACTION 3 OF EXAMPLE I.

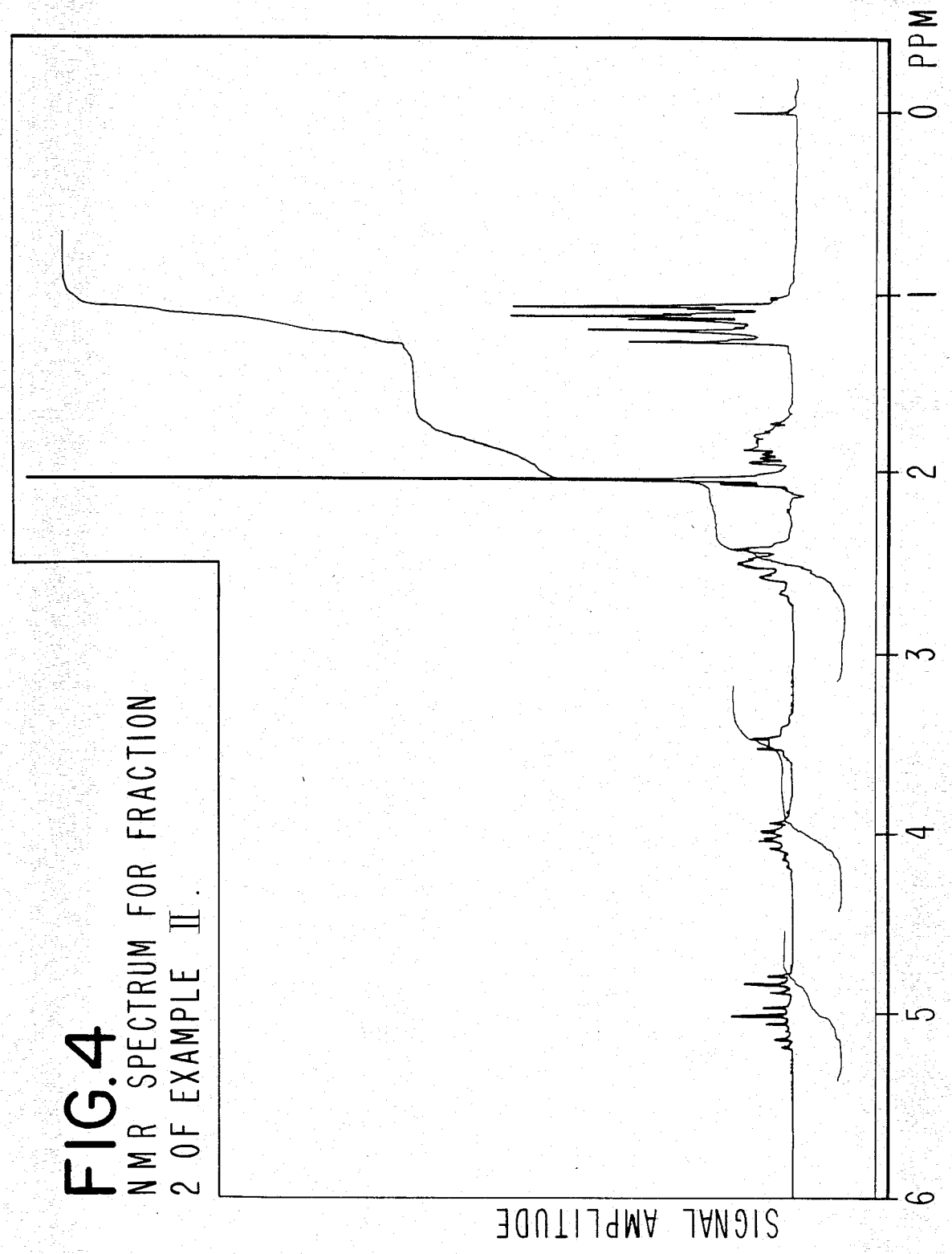

FIG.5
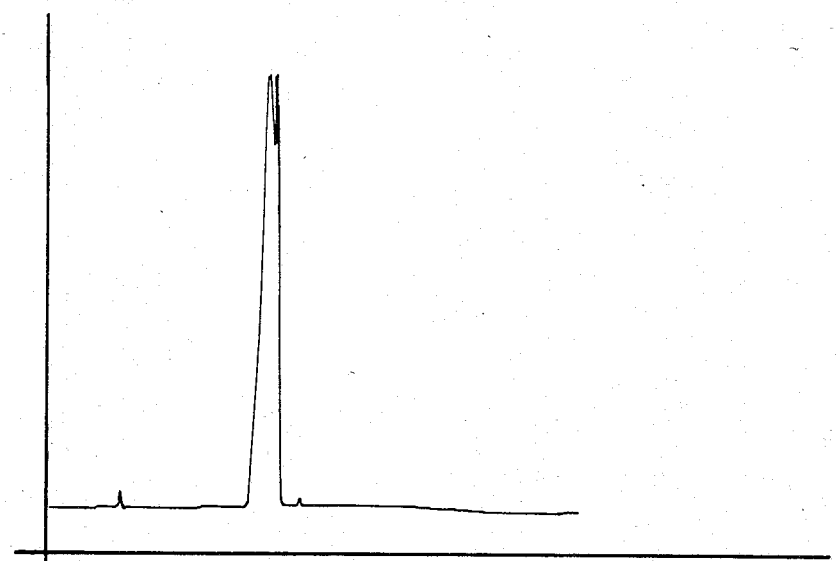
GLC PROFILE FOR FRACTION 2
OF EXAMPLE III.
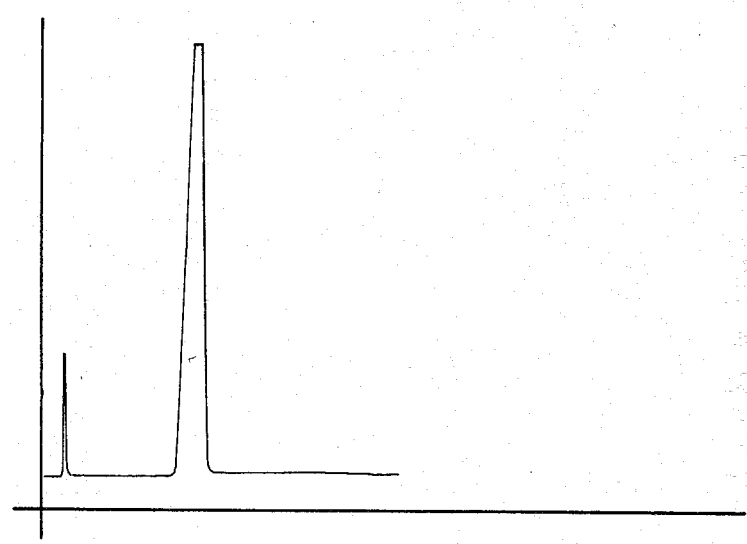
GLC PROFILE FOR FRACTION 2
OF EXAMPLE IV.
FIG.7

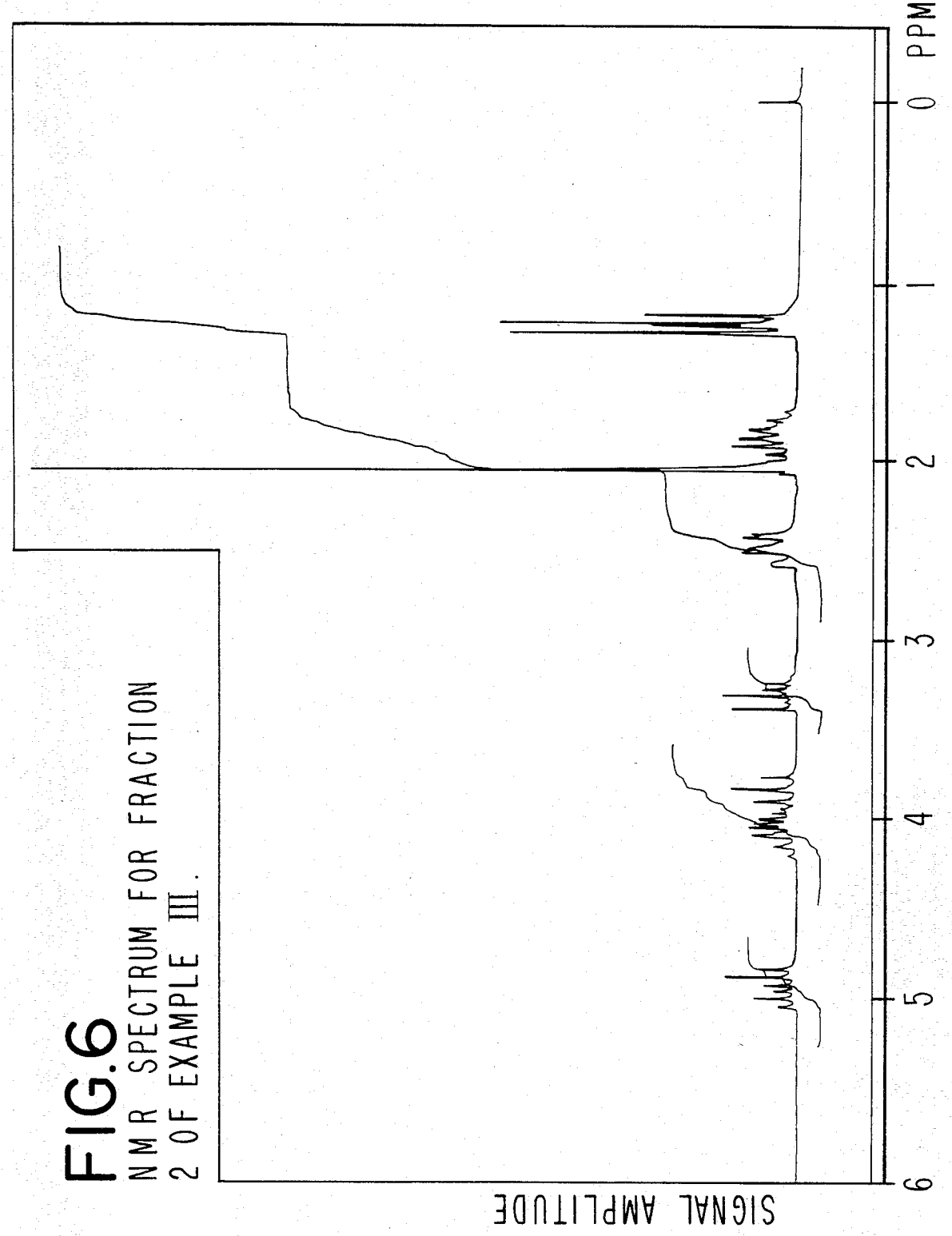
FIG. 6 NMR SPECTRUM FOR FRACTION 2 OF EXAMPLE III.

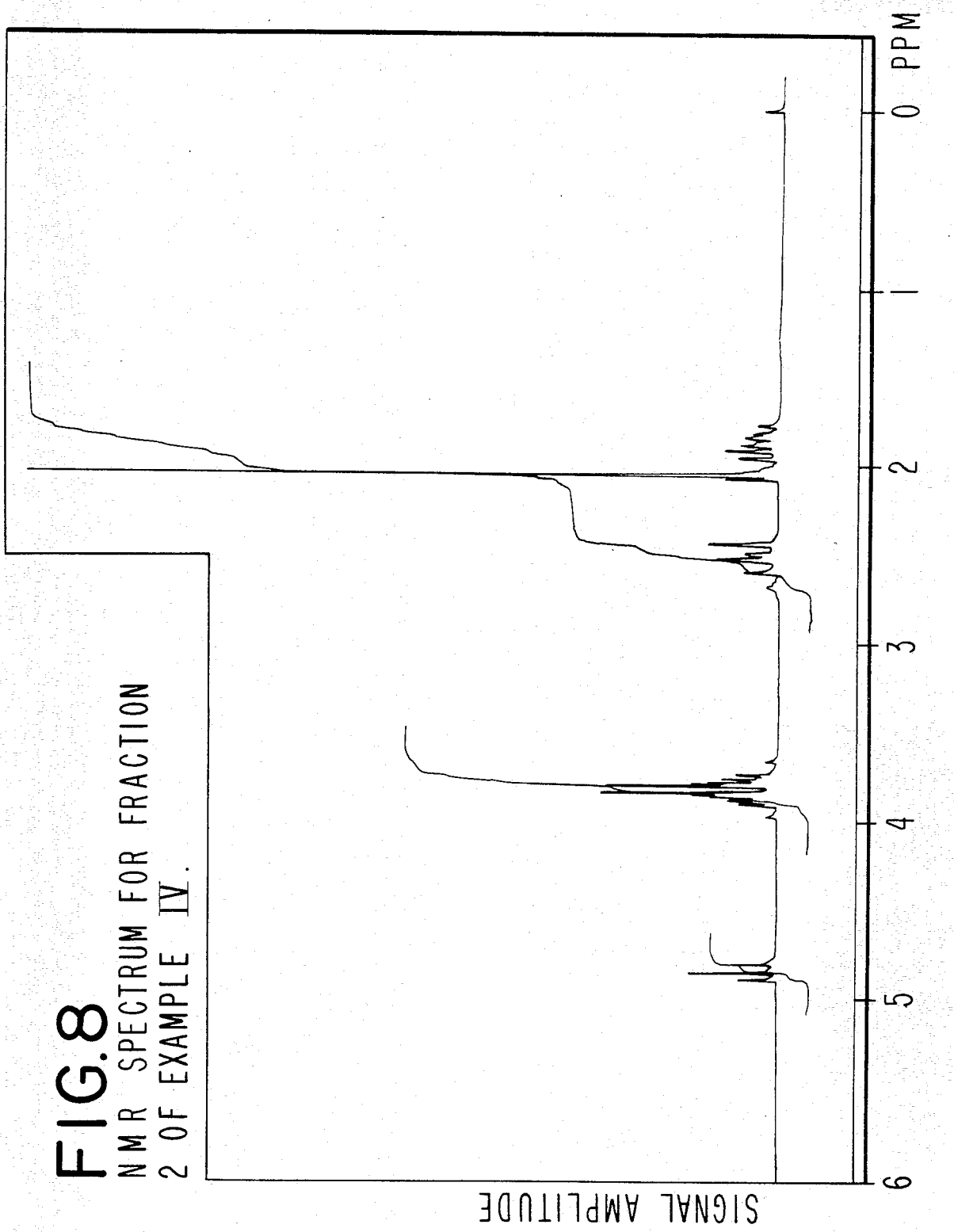
FIG. 8 NMR SPECTRUM FOR FRACTION 2 OF EXAMPLE IV.

FIG.9
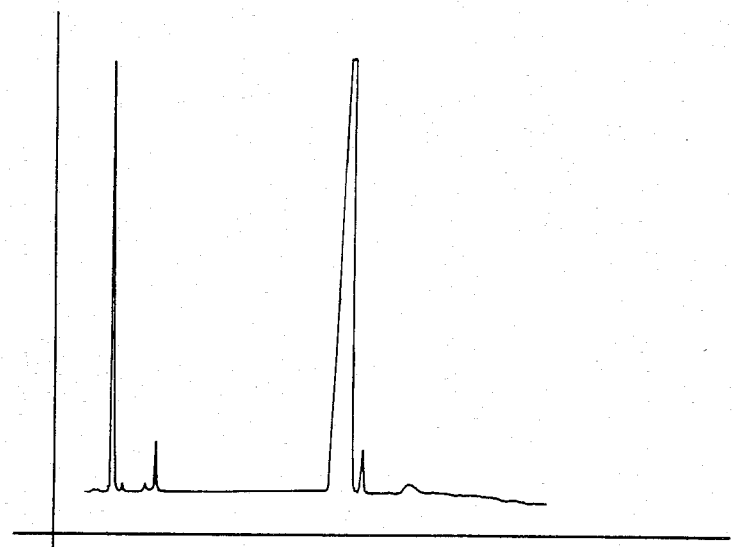
GLC PROFILE FOR EXAMPLE V.
CRUDE
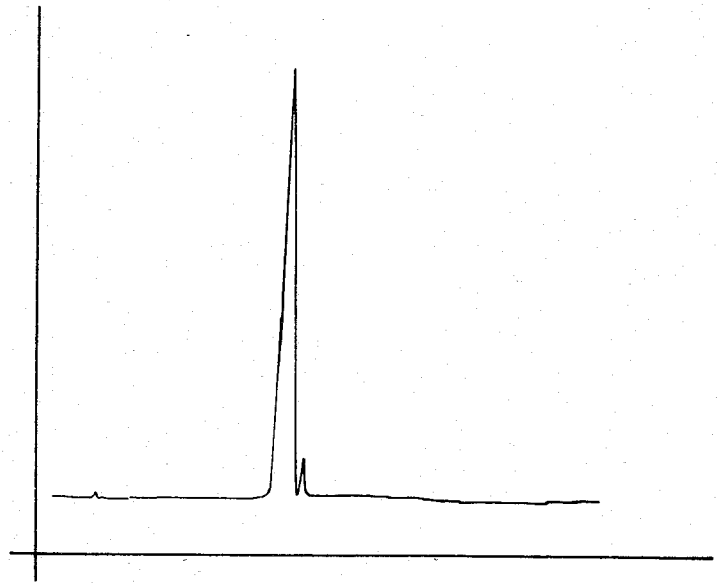
GLC PROFILE FOR FRACTION 3
OF EXAMPLE V.
FIG.10

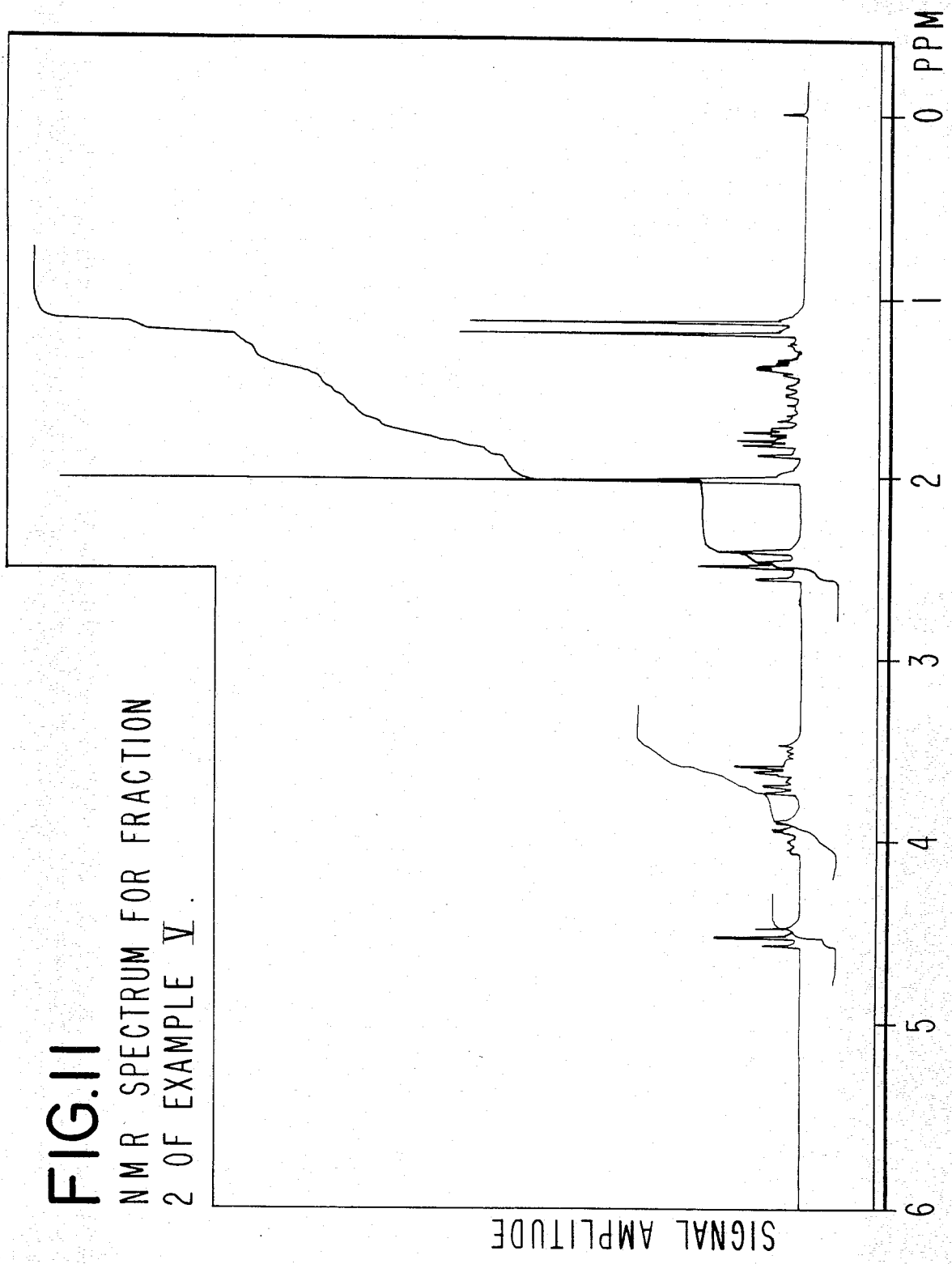
FIG. 11 NMR SPECTRUM FOR FRACTION 2 OF EXAMPLE V.

4,5-DIMETHYL-2-(2-METHYLTHIO)ETHYL)-1,3-OXATHIOLANE

BACKGROUND OF THE INVENTION

This invention provides methyl(methylthioethyl)-1,3-dioxolanes and oxathiolanes defined according to the generic structure:

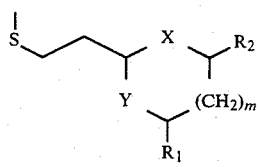

wherein X and Y represent sulphur or oxygen with the proviso that at least one of X and Y is oxygen; wherein m is 0 or 1; and wherein $R_1$ and $R_2$ are the same or different and each represent hydrogen or methyl and uses thereof in augmenting or enhancing the aroma or taste of foodstuffs.

Artificial flavoring agents for foodstuffs have received increasing attention in recent years. In many areas, such food flavoring agents are preferred over natural flavoring agents at least in part because of the uniform flavor that may be so obtained. For example, natural food flavoring agents such as extracts, essences, concentrates and the like are often subject to wide variation due to changes in the quality, type and treatment of the raw materials. Such variation can be reflected in the end product and results in unreliable flavor characteristics and uncertainty as to consumer acceptance and cost. Additionally, the presence of the natural product in the ultimate food may be undesirable because of increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the mechanism for flavoring development in many foods is not understood. This is notable in products having beef broth-like, meat extract-like, hydrolyzed vegetable protein-like, roasted, pot roast, meaty, bloody, oniony, garlic, buttery and mushroom-like taste and aroma nuances.

Reproduction of beef broth-like, meat extract-like, hydrolyzed vegetable protein-like, roasted, pot roast-like, meaty, bloody, oniony, garlic, buttery and mushroom aroma and taste nuances has been the subject of a long and continuous search by those engaged in the production of foodstuffs. The severe shortage of food, especially protein foods, in many parts of the world has given rise to the need for utilizing non-meat sources of proteins and making such proteins as palatable and as meat-like as possible. Hence, materials which will closely simulate or exactly reproduce the flavor and aroma of beef broth, hydrolyzed vegetable protein, yeast, meat, chicken soup, bread, garlic, onion and even pineapple and tomato are required. Furthermore, meat flavors and vegetable flavors have been enhanced previously by the use of such materials as monosodium glutamate. In many diets sodium is not desired. Furthermore, in many diets, the use of the glutamate ion or glutamic acid is not desired. Therefore a need has arisen for a monosodium glutamate replacer which does not have any glutamate ion present.

Moreover, there are a great many meat containing or meat based foods presently distributed in a preserved form. Examples of these are condensed soups, dry soup mixes, dry meat, freeze dried or lyophilized meats, packaged gravies and the like. While these products contain meat or meat extracts, the fragrance, taste and other organoleptic factors are often impaired by the processing operation and it is desirable to supplement or enhance the flavors of these preserved foods with versatile materials which have beef broth-like, meat extract-like, hydrolyzed vegetable protein-like, roasted, pot roast-like, meaty, bloody, onion, garlic and mushroom aroma and taste nuances.

Food flavors in the alkylthioalkanal area are known in the prior art. Thus, various 4-(methylthio)-butanal itself defined according to the structure:

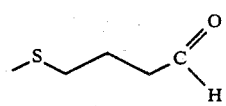

and the diethyl acetal thereof are known for augmenting or enhancing the aroma or taste of foodstuffs and other consumable materials as is taught in U.S. Pat. No. 3,904,556 issued on Sept. 9, 1975 (the specification of which is incorporated by reference herein). Thus, the compound 4-(methylthio)-butanal diethyl acetal is taught in said U.S. Pat. No. 3,904,556 to provide a mushroom, heated onion flavor with green sweet tomato, oniony and garlic nuances. The 4-(methylthio)-butanal itself is taught by said U.S. Pat. No. 3,904,556 to provide a mushroom-like, tomato-like, vegetable-like, cheesey and fruity taste.

Alkanes having 3-methylthio moieties are known in the prior art, for example, that disclosed in Chem. Abstracts, Volume 96, No. 103327y having the structure:

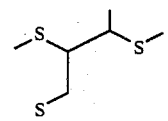

This abstract is of Tetrahedron Letters, Vol. 22, number 42, pages 4159–4162, 1981, (Title: "Thiosulfonium Ions. Methylthiolation of 3-methylthio-1-butene and cis- and trans-1-methylthio-2-butene": Kim and Caserio).

Chem. Abstracts, Vol. 96:20080m which is an abstract of Fischer, Liebigs Ann. Chem., 1981 (10), 1899–1902 discloses the compound having the structure:

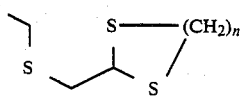

wherein n is 2, 3 or 4 but does not disclose its organoleptic utilities.

Chem. Abstracts, Vol. 84:164792v, (abstract of German Offenlegungsschrift No. 2,530,273) discloses the compound having the structure:

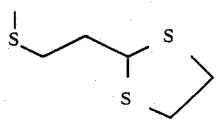

but does not disclose its organoleptic utilities.

U.S. Pat. No. 4,153,442 issued on May 8, 1979; U.S. Pat. No. 4,224,051 issued on Sept. 23, 1980; and U.S. Pat. No. 4,101,307 issued on June 18, 1978 each discloses plant growth regulating materials compounds defined according to the generic structure:

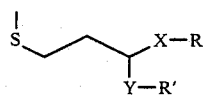

in which
X and Y which may be the same or different and represent oxygen, sulphur or a radical N—B where B is hydrogen, a lower alkyl radical containing 1 to 4 carbon atoms, an optionally substituted aryl radical or an optionally substituted acyl radical containing from 1 to 4 carbon atoms;
R and R' which may be the same or different and represent a lower alkyl radical containing from 1 to 4 carbon atoms or an acyl or amido radical containing from 1 to 4 carbon atoms; in addition they may form with

a cycle corresponding to the formula

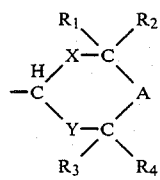

in which
$R_1$, $R_2$, $R_3$ and $R_4$ which may be the same or different and represent hydrogen, an alkyl radical containing from 1 to 4 carbon atoms and optionally substituted by a halogen, the radicals $NO_2$, hydroxy or alkoxy containing from 1 to 4 carbon atoms;
A represents either a single bond or an alkylene chain containing from 1 to 4 carbon atoms optionally interrupted by an oxygen atom or a group N—B' where B' represents hydrogen, an optionally halogenated or hydroxylated alkyl group, an acyl group, the hydrocarbon portion of these radicals containing from 1 to 4 carbon atoms, or a cycle having in common with the preceding cycle 1 to 2 carbon atoms and containing from 3 to 6 carbon atoms, from 0 to 2 oxygen atoms and/or a group N—B, or a cycle corresponding to the formula

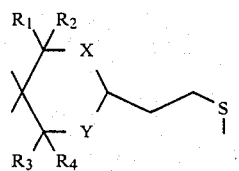

Included in this generic structure is the genus defined according to the structure:

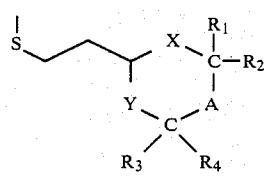

Specific compounds set forth in U.S. Pat. Nos. 4,153,442, 4,224,051 and 4,101,307 are those having the structure:

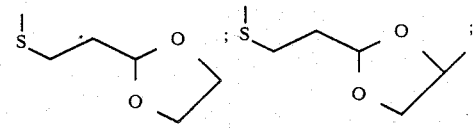

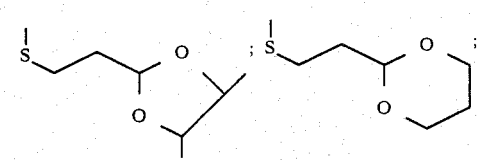

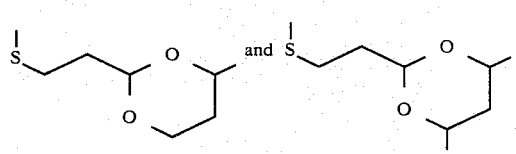

However, these patents do not specifically disclose the compound having the structure:

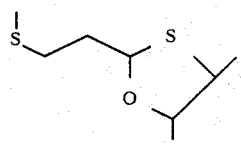

These patents also do not set forth the criticality of these compounds insofar as their organoleptic utilities are concerned nor do they disclose any organoleptic utilities of such compounds.

Nagao, et al, Tetrahedron Letters No. 34, pages 3167–3168 (1979) discloses the genus of compounds defined according to the structure:

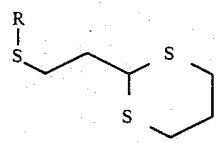

in a synthetic route to yield certain ketones. In this genus R may be methyl, ethyl, propyl, butyl, tolyl, tolyl methoxy, allyl or phenyl. This genus is not part of the instant invention. Furthermore, the Nagao, et al paper does not disclose the organoleptic uses of such compounds.

BRIEF DESCRIPTION OF THE DRAWINGS

FIG. 1 is the GLC profile for fraction 3 of the distillation product of the reaction product of Example I containing the compound having the structure:

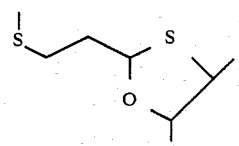

(conditions: 10'×0.125" SE-30 column programmed at 100°–220° C. at 8° C. per minute).

FIG. 2 is the NMR spectrum for fraction 3 of the distillation product of the reaction product of Example I containing the compound having the structure:

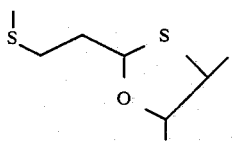

(conditions: Field strength: 100 MHz; Solvent: $CFCl_3$).

FIG. 3 is the GLC profile for fraction 2 of the distillation product of the reaction product of Example II containing the compound having the structure:

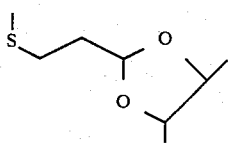

(conditions: 10'×0.125" SE-30 column programmed at 100°–220° C. at 8° C. per minute).

FIG. 4 is the NMR spectrum for fraction 2 of the distillation product of the reaction product of Example II containing the compound having the structure:

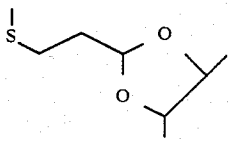

(conditions: Field Strength: 100 MHz; Solvent: $CFCl_3$).

FIG. 5 is the GLC profile for fraction 2 of the distillation product of the reaction product of Example III containing the compound having the structure:

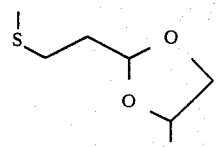

(conditions: 10'×0.125" SE-30 column programmed at 100°–220° C. at 8° C. per minute).

FIG. 6 is the NMR spectrum for fraction 2 of the distillation product of the reaction product of Example III containing the compound having the structure:

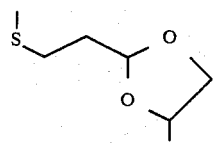

(conditions: Field Strength: 100 MHz; Solvent: $CFCl_3$).

FIG. 7 is the GLC profile for fraction 2 of the distillation product of the reaction product of Example IV containing the compound having the structure:

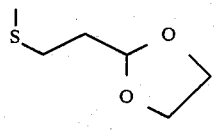

(conditions: 10'×0.125" SE-30 column programmed at 100°–220° C. at 8° C. per minute).

FIG. 8 is the NMR spectrum for fraction 2 of the distillation product of the reaction product of Example IV containing the compound having the structure:

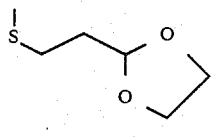

(conditions: Field Strength: 100 MHz; Solvent: $CFCl_3$).

FIG. 9 is the GLC profile for the crude reaction product of Example V containing the compound having the structure:

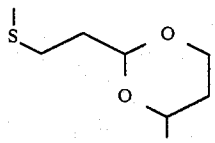

(conditions: SE-30 column programmed at 100°–220° C. at 8° C. per minute).

FIG. 10 is the GLC profile for fraction 3 of the distillation product of the reaction product of Example V containing the compound having the structure:

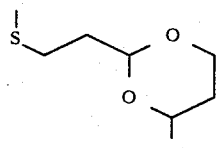

(conditions: 10'×0.125" SE-30 column programmed at 100°–220° C. at 8° C. per minute).

FIG. 11 is the NMR spectrum for fraction 2 of the distillation product of the reaction product of Example V containing the compound having the structure:

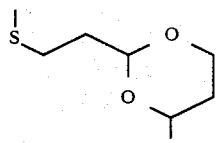

(conditions: Field Strength: 100 MHz; Solvent: CFCl$_3$).

THE INVENTION

The present invention provides methyl(methylthioethyl)-1,3-dioxolanes and oxathiolanes useful for augmenting or enhancing the aroma or taste of foodstuffs, said methyl(methylthioethyl)-1,3-dioxolanes and oxathiolanes being defined according to the structure:

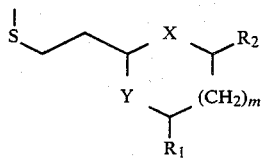

wherein X and Y represent sulphur or oxygen with the proviso that at least one of X and Y is oxygen; wherein m is 0 or 1; and wherein R$_1$ and R$_2$ are the same or different and each represent hydrogen or methyl as well as methods for augmenting or enhancing or modifying the organoleptic properties, e.g. taste and aroma, of said foodstuffs.

The methyl(methylthioethyl)-1,3-dioxolanes and oxathiolanes of our invention augment or enhance beef broth-like, meat extract-like, hydrolyzed vegetable protein-like, roasted, pot roast-like, meaty, bloody, oniony, garlic, buttery and mushroom aroma and taste nuances making them useful for augmenting or enhancing flavors for such foodstuffs as beef broth, hydrolyzed vegetable protein, yeast, meat, chicken soup, bread, pineapple, tomato, garlic, onion, butter and mushroom flavored foodstuffs.

The methyl(methylthioethyl)-1,3-dioxolanes and oxathiolanes of our invention defined according to the structure:

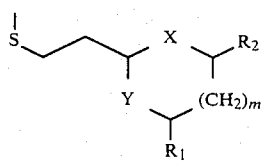

wherein X and Y represent sulphur or oxygen with the proviso that at least one of X and Y is oxygen; wherein m is 0 or 1; and wherein R$_1$ and R$_2$ are the same or different and each represent hydrogen or methyl may be produced by means of reacting an alpha,beta-diol or an alpha,gamma-diol or an alpha,beta-hydroxythiol, or an alpha,gamma-hydroxythiol defined according to the structure:

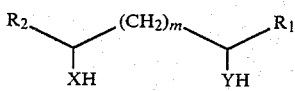

wherein X and Y each represent sulphur or oxygen with at least one of X or Y being oxygen; wherein m represents 0 or 1; and wherein R$_1$ and R$_2$ are the same or different and each represents hydrogen or methyl with methional having the structure:

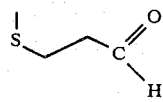

in the presence of a protonic acid catalyst such as para-toluene sulfonic acid, xylene sulfonic acid, methane sulfonic acid, phosphoric acid and concentrated sulfuric acid. The reaction takes place in the presence of a solvent having a boiling point such that the reaction can proceed in a reasonable period of time, e.g. 1–12 hours at atmospheric pressure or pressures somewhat greater than atmospheric pressure (up to 10 atmospheres). The reaction temperature may vary from between about 70° C. up to about 140° C. Reaction temperatures greater than 140° C. give rise to unnecessary breakdown of reaction product. Reaction temperatures lower than 70° C. give rise to too long a period of time of reaction. The solvents utilized must be inert to the reaction product as well as inert to the reactants. The solvents utilized must also have boiling points of between 70° C. and 140° C. since the reaction is to take place under reflux conditions. The reaction solvent must also be capable of being completely removed from the product on distillation in view of the fact that the reaction products are used as food flavors for internal consumption. Accordingly, suitable solvents are, for example, cyclohexane, cyclopentane, cyclooctane, 1-methylcyclohexane, 1,2-dimethylcyclohexane, 1,2,4-trimethylcyclohexane, 2-ethyltetrahydrofuran, 2,5-dimethyltetrahydrofuran and the like.

Examples of the products of our invention and their organoleptic properties are as follows:

TABLE I

| Structure of Compound | Organoleptic Properties |
|---|---|
| 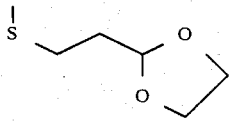 | A beef broth-like, meat extract-like, hydrolyzed vegetable protein-like, roasted and pot roast aroma and taste profile with a "monosodium glutamate-like" effect at a level of 0.01 ppm causing it to be useful in beef broth, hydrolyzed vegetable protein, yeast, meat, chicken soup and bread flavored foods. |

TABLE I-continued

| Structure of Compound | Organoleptic Properties |
|---|---|
| (structure: S—CH2—CH2—CH(O—)(O—)—CH3 with dioxolane ring) | A meaty, hydrolyzed vegetable protein-like aroma with a hydrolyzed vegetable protein-like taste at 0.1 ppm causing it to be useful in meat, hydrolyzed vegetable protein, pineapple and tomato flavored foodstuffs. |
| (similar dioxolane structure) | A bloody, roasted, hydrolyzed vegetable protein-like/meaty aroma with bloody, roasted, hydrolyzed vegetable protein-like and cocoa taste nuances at 0.1 ppm causing it to be useful in meat, hydrolyzed vegetable protein, yeast and bread flavored foodstuffs. |
| (oxathiolane structure with S and O) | An oniony, hydrolyzed vegetable protein-like and garlic aroma and taste profile at 0.1 ppm causing it to be useful in garlic and onion flavored foodstuffs. |
| (dioxane-type structure) | A buttery, roasted, meaty and mushroom-like aroma with buttery, roasted and hydrolyzed vegetable protein-like taste profile at 5 ppm causing it to be useful in butter, mushroom and hydrolyzed vegetable protein flavored foodstuffs. |

At the end of the reaction as stated supra, the reaction product is extracted from the reaction mass or the reaction mass is washed, for example, with saturated sodium chloride. The reaction product is then distilled preferably by means of vacuum distillation.

Thus, the methyl(methylthioethyl)-1,3-dioxolanes and oxathiolanes produced according to our invention can be used to alter, vary, fortify, modify, enhance or otherwise improve the organoleptic properties, including flavor and/or aroma of a wide variety of materials which are ingested, consumed or otherwise organoleptically sensed.

The term "alter" in its various forms will be understood herein to mean the supplying or imparting of a flavor character or note to an otherwise bland, relatively tasteless substance or augmenting an existing flavor characteristic where the natural flavor is deficient in some regard or supplementing the existing flavor or aroma impression to modify the organoleptic character. The materials which are so altered are generally referred to herein as consumable materials.

Such methyl(methylthioethyl)-1,3-dioxolanes and oxathiolanes of our invention are accordingly useful in flavoring compositions. Flavoring compositions are herein taken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

When the methyl(methylthioethyl)-1,3-dioxolanes and oxathiolanes according to this invention are used in a food flavoring composition, they can be combined with conventional flavoring materials or adjuvants. Such co-ingredients or flavoring adjuvants are well known in the art for such use and have been extensively described in the literature. Apart from the requirement that any such adjuvant material is ingestibly acceptable, and thus non-toxic or otherwise non-deleterious, conventional materials can be used and broadly include other flavor materials, vehicles, stabilizers, thickeners, surface active agents, conditioners and flavor intensifiers.

Examples of preferred co-flavoring adjuvants are:
Methyl thiazole alcohol (4-methyl-5-beta-hydroxyethyl thiazole);
2-Methyl butanethiol;
4-Mercapto-2-butanone;
3-Mercapto-2-pentanone;
1-Mercapto-2-propanone;
Benzaldehyde;
Furfural;
Furfural alcohol;
2-Mercapto propionic acid;
Alkyl pyrazine;
Methyl pyrazine;
2-Ethyl-3-methyl pyrazine;
Tetramethyl pyrazine;
Polysulfides;
Dipropyl disulfide;
Methyl benzyl disulfide;
Alkyl thiophenes;
2-Butyl thiophene;
2,3-Dimethyl thiophene;
5-Methyl furfural;
Acetyl furan;
2,4-Decadienal;
Guiacol;
Phenyl acetaldehyde;
δ-Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Monopotassium glutamate;
Sulphur-containing amino acids, e.g. cysteine;
Hydrolyzed vegetable protein;
2-Methylfuran-3-thiol;
2-Methyldihydrofuran-3-thiol;
2,5-dimethylfuran-3-thiol;
Hydrolyzed fish protein; and
Tetramethyl pyrazine.

The methyl(methylthioethyl)-1,3-dioxolanes and oxathiolanes or the compositions incorporating them, as mentioned above, can be combined with one or more vehicles or carriers for adding them to the particular product. Vehicles can be edible or otherwise suitable materials such as ethyl alcohol, propylene glycol, water and the like. Carriers include materials such as gum arabic, carrageenan, other gums and the like. The methyl(methylthioethyl)-1,3-dioxolanes and oxathiolanes according to this invention can be incorporated with the carriers by conventional means such as spray-drying, drum-drying and the like. Such carriers can also include materials for coacervating the methyl(methylthioethyl)-1,3-dioxolanes and oxathiolanes (and other flavoring ingredients, as present) to provide encapsulated products. When the carrier is an emulsion, the flavoring composition can also contain emulsifiers such as mono- and diglycerides or fatty acids and the like. With these carriers or vehicles, the desired physical form of the composition can be prepared.

The quantity of methyl(methylthioethyl)-1,3-dioxolanes and oxathiolanes utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff; the amount and type of flavor initially present in the foodstuff; and further process or treatment steps to which the foodstuff will be subjected; regional and other preference factors; the type of storage, if any, to which the product will be subject; and the preconsumption treatment, such as baking, frying and so on, given to the product by the ultimate consumer. Accordingly, the terminology "effective amount" and "sufficient amount" is understood in the context of the present invention to be quantitatively adequate to alter the flavor of the foodstuff.

It is accordingly preferred that the ultimate composition contain from about 0.001 parts per million (ppm) to about 250 ppm of methyl(methylthioethyl)-1,3-dioxolanes and oxathiolanes or mixtures thereof. More particularly, in food compositions it is desirable to use from about 0.001 ppm to 100 ppm for enhancing flavors and in certain preferred embodiments of the invention, from about 0.001 to 50 ppm of the derivatives are included to add positive flavors to the finished product.

The amount of methyl(methylthioethyl)-1,3-dioxolanes and oxathiolanes or mixtures thereof of our invention to be utilized in flavoring compositions can be varied over a wide range depending upon the particular quality to be added to the foodstuff. Thus, amounts of one or more derivatives according to the present invention of from about 0.05 ppm up to 80 or 90 percent of the total flavoring composition can be incorporated in such compositions. It is generally found to be desirable to include from about 0.05 ppm up to about 0.1 percent of the methyl(methylthioethyl)-1,3-dioxolanes and oxathiolanes in such compositions.

The following examples are given to illustrate embodiments of the invention as it is preferred to practice it. It will be understood that these examples are illustrative and the invention is not to be considered as restricted thereto except as indicated in the appended claims.

All parts, proportions, percentages and ratios used herein are by weight unless otherwise indicated.

EXAMPLE I

PREPARATION OF 4,5-DIMETHYL-2-[2-(METHYLTHIO)ETHYL]-1,3-OXATHIOLANE

Reaction:

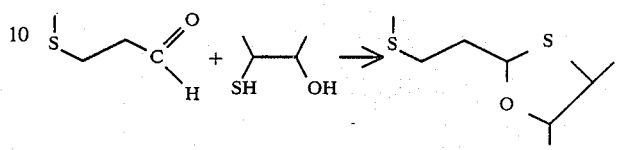

Into a 100 ml reaction flask equipped with spin bar, reflux condenser, heating mantle, hot plate apparatus (with magnetic stirring apparatus) is placed 5 ml cyclohexane, 0.2 grams paratoluenesulfonic acid and 5.3 grams (0.05 moles) of 3-mercapto-2-butanol. Over a period of 30 minutes, 5.2 grams (0.05 moles) of 3-methylthiopropionaldehyde are added to the reaction mass. The reaction mass is then heated to reflux and water of reaction is continuously removed during the refluxing of the reaction mass. The reaction takes place over a period of 7 hours. At the end of the 7 hours the reaction mass is transferred to a separatory funnel and the reaction mass is washed with one 50 ml portion of saturated aqueous sodium chloride solution and then dried over anhydrous sodium sulfate. The product is then filtered and distilled on a Microvigreux column yielding the following fractions:

| Fraction Number | Vapor Temp. (°C.) | Liquid Temp. (°C.) | Vacuum mm/Hg. |
|---|---|---|---|
| 1 | 103 | 111 | 2 |
| 2 | 105 | 113 | 2 |
| 3 | 105 | 114 | 2 |
| 4 | 100 | 120 | 2 |

FIG. 1 is the GLC profile for fraction 3 of the above distillation containing the compound having the structure:

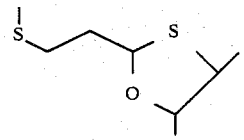

(conditions: 10'×0.125" SE-30 column programmed at 100°-220° C. at 8° C. per minute).

FIG. 2 is the NMR spectrum for fraction 3 of the foregoing distillation containing the compound having the structure:

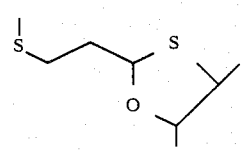

(conditions: Field Strength: 100 MHz; Solvent: CFCl$_3$).

EXAMPLE II

PREPARATION OF 4,5-DIMETHYL-2-[2-(METHYLTHIO)ETHYL]-1,3-DIOXOLANE

Reaction:

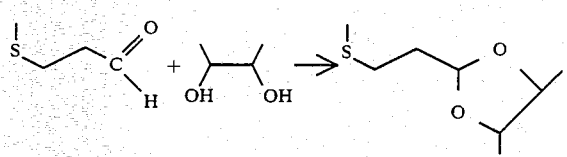

Into a 100 ml reaction flask equipped with spin bar, reflux condenser, heating mantle and hot plate with magnetic stirring apparatus is placed 5 ml cyclohexane, 0.2 grams para-toluenesulfonic acid and 3.5 grams (0.04 moles) of 2,3-butanediol. Over a period of 30 minutes, 4.1 grams (0.04 moles) of 3-methylthiopropionaldehyde is added to the reaction mass. The reaction mass is then heated to reflux and refluxed for a period of 7 hours during which water of reaction is removed.

The reaction mass is transferred to a separatory funnel and washed with one 50 ml portion of saturated sodium chloride solution and then dried over anhydrous sodium sulfate, filtered and distilled on a Microvigreux column yielding the following two fractions:

| Fraction Number | Vapor Temp. (°C.) | Liquid Temp. (°C.) | Vacuum mm/Hg |
|---|---|---|---|
| 1 | 78 | 86 | 2 |
| 2 | 76 | 90 | 2 |

FIG. 3 is the GLC profile for fraction 2 of the foregoing distillation containing the compound having the structure:

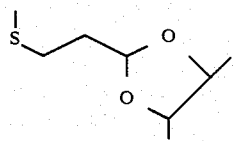

(conditions: 10'×0.125" SE-30 column programmed at 100°–220° C. at 8° C. per minute).

FIG. 4 is the NMR spectrum for fraction 2 of the foregoing distillation containing the compound having the structure:

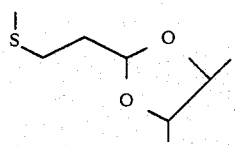

(conditions: Field Strength: 100 MHz; Solvent: CFCl₃).

EXAMPLE III

PREPARATION OF 4-METHYL-2-[2-(METHYLTHIO)ETHYL]-1,3-DIOXOLANE

Reaction:

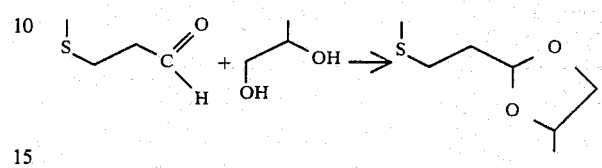

Into a 100 ml reaction flask equipped with spin bar, reflux condenser, heating mantle and hot plate with magnetic stirring apparatus is placed 5 ml cyclohexane, 0.2 grams para-toluenesulfonic acid and 3.8 grams (0.05 moles) of 1,2-propanediol. Over a period of 8 hours, 3-methylthiopropionaldehyde is added to the reaction mass. The reaction mass is then heated to reflux and during refluxing water of formation is removed. The refluxing continues for a period of 7 hours. At the end of the 7 hour period, the reaction mass is transferred to a separatory funnel and washed with one 50 ml portion of saturated aqueous sodium chloride solution and then dried over anhydrous sodium sulfate, filtered and distilled on a Microvigreux column yielding the following fractions:

| Fraction Number | Vapor Temp. (°C.) | Liquid Temp. (°C.) | Vacuum mm/Hg. |
|---|---|---|---|
| 1 | 79 | 85 | 2 |
| 2 | 79 | 87 | 2 |
| 3 | 75 | 90 | 2 |

FIG. 5 is the GLC profile for fraction 2 of the foregoing distillation containing the compound having the structure:

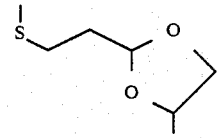

(conditions: 10'×0.125" SE-30 column programmed at 100°–220° C. at 8° C. per minute).

FIG. 6 is the NMR spectrum for fraction 2 of the foregoing distillation containing the compoound having the structure:

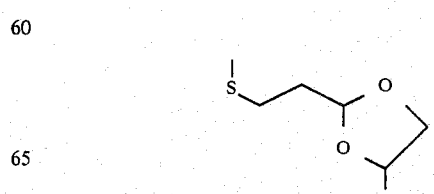

(conditions: Field Strength: 100 MHz; Solvent: CFCl₃).

EXAMPLE IV

PREPARATION OF 2-[2-(METHYLTHIO)ETHYL]-1,3-DIOXOLANE

Reaction:

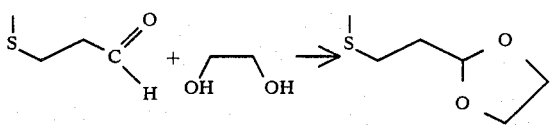

Into a 100 ml reaction flask equipped with spin bar, reflux condenser, heating mantle and hot plate with magnetic stirring apparatus is placed 5 ml cyclohexane, 0.2 grams para-toluenesulfonic acid and 3.1 grams (0.05 moles) of 1,2-ethanediol. Over a period of 30 minutes, 5.2 grams (0.05 moles) of 3-methylthiopropionaldehyde is added to the reaction mass. The reaction mass is then heated to reflux and during reflux, water of formation is removed. The refluxing continues for a period of 9 hours. At the end of the 9 hour period, the reaction mass is cooled and transferred to a separatory funnel and washed with one 50 ml portion of saturated sodium chloride solution. The reaction mass is then dried over anhydrous sodium sulfate, filtered and distilled on a Microvigreux column yielding the following fractions:

| Fraction Number | Vapor Temp. (°C.) | Liquid Temp. (°C.) | Vacuum mm/Hg. |
|---|---|---|---|
| 1 | 72 | 80 | 2 |
| 2 | 65 | 90 | 2 |

FIG. 7 is the GLC profile for fraction 2 of the foregoing distillation containing the compound having the structure:

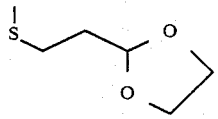

(conditions: 10' × 0.125" SE-30 column programmed at 100°–220° C. at 8° C. per minute).

FIG. 8 is the NMR spectrum for fraction 2 of the foregoing distillation containing the compound having the structure:

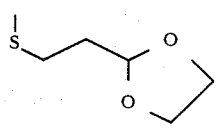

(conditions: Field Strength: 100 MHz; Solvent: CFCl₃).

EXAMPLE V

PREPARATION OF 4-METHYL-2-[2-(METHYLTHIO)ETHYL]-m-DIOXANE

Reaction:

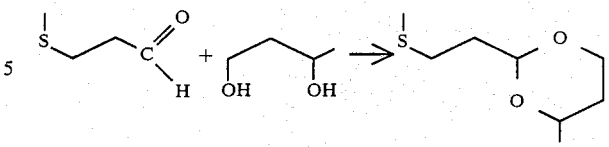

Into a 100 ml reaction flask equipped with spin bar, reflux condenser, heating mantle and hot plate with magnetic stirring apparatus is placed 0.2 grams para-toluenesulfonic acid, 5 ml cyclohexane and 4.5 grams of 1,3-butanediol. Slowly added to the reaction mass over a period of 30 minutes is 3-methylthiopropionaldehyde (5.2 grams; 0.05 moles). The reaction mass is then heated to reflux and refluxed for a period of 9 hours. During the refluxing process, water of reaction is removed from the reaction mass. At the end of the 9 hour refluxing period, the reaction mass is then cooled and transferred to a separatory funnel and washed with one 50 ml portion of saturated sodium chloride solution and then dried over anhydrous sodium sulfate, filtered and distilled on a Microvigreux column yielding the following fractions:

| Fraction Number | Vapor Temp. (°C.) | Liquid Temp. (°C.) | Vacuum mm/Hg |
|---|---|---|---|
| 1 | 85 | 95 | 2 |
| 2 | 90 | 96 | 2 |
| 3 | 80 | 110 | 2 |

FIG. 9 is the GLC profile for the crude reaction product prior to distillation containing the compound having the structure:

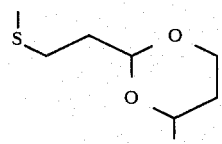

(conditions: SE-30 column programmed at 100°–220° C. at 8° C. per minute).

FIG. 10 is the GLC profile for fraction 3 of the foregoing distillation containing the compound having the structure:

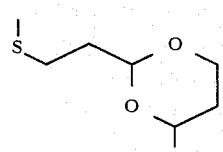

(conditions: 10' × 0.125" SE-30 column programmed at 100°–220° C. at 8° C. per minute).

FIG. 11 is the NMR spectrum for fraction 2 of the foregoing distillation containing the structure:

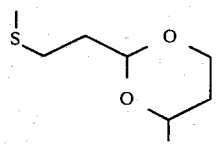

(conditions: Field Strength: 100 MHz; Solvent: CFCl₃).

EXAMPLE VI

The compound having the structure:

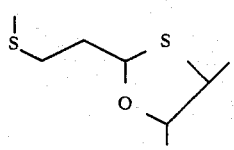

produced according to Example I is added to a 2% solution of Wyler's "Beef Flavored Instant Bouillon" (manufactured by Wyler Foods, Division of Borden, Inc., Chicago, Ill.)

(Ingredients: salt, hydrolyzed vegetable protein, malto dextrin, sugar, beef fat, water, monosodium glutamate, flavorings, corn sugar, beef extract, caramel color, hydrogenated vegetable fat and U.S. certified food color)

at the rate of 0.1 ppm. The resulting flavor can be described as "beef with onion and garlic aroma and taste nuances". The onion and garlic taste nuances are enhanced by the addition at the rate of 0.3 ppm of allyl propyl disulfide or allyl propyl trisulfide. The meaty nuances are enhanced by the addition of the compound having the structure:

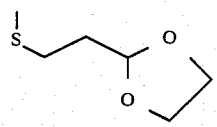

prepared according to Example IV at the rate of 0.04 ppm. When the compound having the structure:

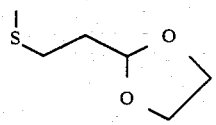

is added thusly, the "savory" nuances are enhanced and a beef broth-like, meat extract-like, hydrolyzed vegetable protein-like, roasted and pot roast-like aroma and taste of great intensity is imparted to the soup. The compound having the structure:

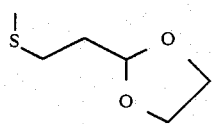

is an excellent replacer for monosodium glutamate. Indeed, the monosodium glutamate in the ingredient grouping may be completely removed when the compound having the structure:

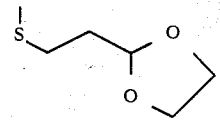

is added even at levels as low as 0.01 ppm.

EXAMPLE VII

A meat gravy is prepared containing 0.2 ppm by weight of the compound having the structure:

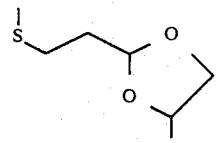

prepared according to Example III, using a beef base and beef fat. The resulting beef gravy is then added to mushrooms cooked using boiling water at a rate of 10 parts gravy to 100 parts cooked mushrooms. The resulting mushroom platter has an excellent natural-like meaty, hydrolyzed vegetable protein-like, savory mushroom flavor. The flavor is even further enhanced when tomato sauce is added to the mixture. The flavor is still more enhanced with 2-n-butylthiazole at the rate of 0.02 ppm is added to the gravy.

EXAMPLE VIII

GRAVY FLAVOR

A gravy flavoring material is prepared by admixing the following ingredients:

| Ingredients | Parts by Weight |
| --- | --- |
| Diacetyl (5% solution in propylene glycol) | 0.20 |
| Furfural | 0.20 |
| 2-acetyl-3-ethyl pyrazine | 1.00 |
| 2-methyl-3-furfuran thiazole | 0.05 |
| Methional | 2.00 |
| 2,5-dimethyl-3-furan thio acetate | 0.80 |

A bench panel of 5 individuals compared the above formulation with one containing the compound having the structure:

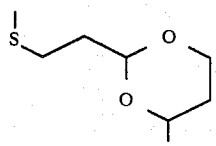

which is added at the rate of 5 ppm.

The flavor with the compound having the structure:

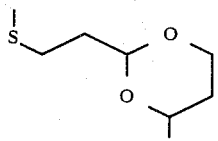

has a roasted, meaty, mushroom aroma and taste profile with pleasant, buttery nuances.

When the flavor which includes the compound having the structure:

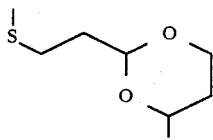

is added at the rate of 0.5% to a standard chicken frankfurter containing 50 parts by weight of chicken and 50 parts by weight of pork, the chicken nuances are intensified 50% more than without the compound having the structure:

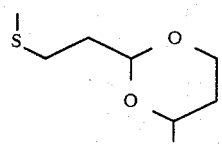

and, in addition, roasted, meaty and mushroom nuances are imparted.

What is claimed is:

1. 2-[2-(methylthio)ethyl]-1,3-oxathiolane having the structure:

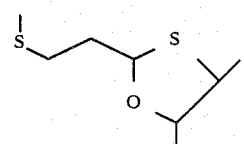

* * * * *